US 7,803,964 B2

(12) United States Patent
Tanaka et al.

(10) Patent No.: US 7,803,964 B2
(45) Date of Patent: Sep. 28, 2010

(54) METHOD FOR SYNTHESIZING T-BUTYL (METH)ACRYLATE

(75) Inventors: Shigeho Tanaka, Hiroshima (JP); Tohru Endoh, Hiroshima (JP); Haruki Sato, Hiroshima (JP); Toshihiro Sato, Hiroshima (JP); Kazutaka Inoue, Hiroshima (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 129 days.

(21) Appl. No.: 11/815,664

(22) PCT Filed: Feb. 6, 2006

(86) PCT No.: PCT/JP2006/301993
§ 371 (c)(1),
(2), (4) Date: Aug. 7, 2007

(87) PCT Pub. No.: WO2006/082965
PCT Pub. Date: Aug. 10, 2006

(65) Prior Publication Data
US 2009/0012327 A1 Jan. 8, 2009

(30) Foreign Application Priority Data
Feb. 7, 2005 (JP) .............................. 2005-030488

(51) Int. Cl.
*C07C 69/52* (2006.01)
(52) U.S. Cl. ..................................................... 560/205
(58) Field of Classification Search ........................ None
See application file for complete search history.

(56) References Cited
U.S. PATENT DOCUMENTS

| 4,012,456 | A |   | 3/1977  | Chaplits |        |
|-----------|---|---|---------|----------|--------|
| 4,036,905 | A |   | 7/1977  | Kornfeld |        |
| 4,208,540 | A | * | 6/1980  | Imaizumi et al. | 585/809 |
| 4,824,998 | A | * | 4/1989  | Inoue et al. | 560/205 |
| 4,873,391 | A | * | 10/1989 | Inoue et al. | 585/639 |

FOREIGN PATENT DOCUMENTS

| JP | 47 13250   | 7/1972  |
|----|------------|---------|
| JP | 54 135710  | 10/1979 |
| JP | 54 138506  | 10/1979 |
| JP | 62 63544   | 3/1987  |
| JP | 63 41431   | 2/1988  |
| JP | 63 135352  | 6/1988  |
| JP | 8 245433   | 9/1996  |

* cited by examiner

*Primary Examiner*—Paul A Zucker
(74) *Attorney, Agent, or Firm*—Oblon, Spivak, McClelland, Maier & Neustadt, L.L.P.

(57) ABSTRACT

Disclosed is a method for synthesizing t-butyl (meth)acrylate at low cost. Specifically, disclosed is a method for synthesizing a carboxylic acid ester by performing an addition reaction between isobutylene and (meth)acrylic acid in the presence of an acidic catalyst. This method includes the steps of:

(A) performing a dehydration decomposition reaction of t-butyl alcohol in the presence of a first acidic catalyst;
(B) obtaining crude isobutylene gas by separating at least water from a produced gas obtained in the step A;
(C) absorbing the crude isobutylene gas in an absorption solvent containing (meth)acrylic acid; and
(D) producing t-butyl (meth)acrylate by performing the addition reaction by bringing the absorption solvent which has absorbed the crude isobutylene gas into contact with a second acidic catalyst.

15 Claims, 5 Drawing Sheets

METHOD FOR SYNTHESIZING T-BUTYL (METH)ACRYLATE

TECHNICAL FIELD

The present invention relates to a method for synthesizing t-butyl (meth)acrylate.

BACKGROUND ART

It is well known that t-butyl (meth)acrylate is not easily synthesized by a dehydration esterification reaction between a carboxylic acid and an alcohol, which is a general synthesizing method of an ester, or by an ester interchange reaction between a (meth)acrylate and t-butyl alcohol. This is because, in the case of the dehydration esterification reaction, t-butyl alcohol, which is a tertiary alcohol, is easily decomposed in the presence of a strong acid, which is a common catalyst, and isobutylene produced is removed from the reaction system simultaneously with the dehydration and hence a reaction producing an ester does not proceed. Further, in the case of the ester interchange reaction, a basic catalyst, a metal alkoxide catalyst or the like is an effective catalyst which can suppress decomposition of t-butyl alcohol, however, a formation of t-butyl ester is suppressed because a t-butyl group in an activated t-butyl alcohol stereochemically obstructs reactivity of a hydroxyl group.

Consequently, it has been conventionally known that an addition reaction between (meth)acrylic acid and isobutylene is effective for a synthesis of t-butyl (meth)acrylate. However, this method is unfavorable in view of cost of raw materials because isobutylene is relatively expensive. As an economical and advantageous method for producing t-butyl (meth)acrylate by reducing the cost of raw materials through suppressing side reactions, a method of suppressing conversion (Patent Document 1) and a method of lowering a reaction temperature (Patent Document 2) are listed. However, expensive isobutylene is still used in these methods, and besides, a countermeasure for a pressurized gas is necessary because isobutylene, which is a raw material, is in many cases used in a pressurized gas state, and hence these methods are economically unfavorable.

On the other hand, various methods for producing isobutylene from t-butyl alcohol, which is an inexpensive raw material, have been known.

For example, a dehydration decomposition reaction of t-butyl alcohol easily occurs to produce isobutylene by using a strongly acidic catalyst in a liquid-phase system and heating the liquid-phase system (Patent Documents 3, 4 and 5).

Further, it has also been well known that a dehydration decomposition reaction of t-butyl alcohol easily occurs to produce isobutylene by contacting gaseous t-butyl alcohol to a solid acid catalyst such as a solid phosphoric acid, an activated alumina or silica-alumina at a high temperature in a gas-phase system (Patent Documents 6 and 7).

However, in any of these methods, vapor pressures of water to be produced, isobutylene dimer, which is a main product by side reactions, and t-butyl alcohol, which is a raw material, are relatively high at a temperature at which the dehydration decomposition reaction is performed effectively, and hence these materials mix in a target isobutylene when isobutylene produced is taken out of the dehydration reaction system as a gas.

Consequently, when the isobutylene gas produced is directly introduced into a step of an addition reaction with (meth)acrylic acid, isobutylene is hydrated again to change into t-butyl alcohol by moisture contained in the isobutylene at an equivalent amount or more. In this case, there has been a problem which is specific in this system and has to be improved, namely, the problem that productivity of a (meth)acrylate reduces because it is very difficult to advance the dehydration esterification reaction between t-butyl alcohol and (meth)acrylic acid as mentioned above.

On the other hand, in the case that isobutylene is isolated in high purity, conduction of a high degree distillation operation or a condensation-separation operation which uses an expensive refrigeration energy is necessary to separate water to be produced and unreacted t-butyl alcohol, and moreover, a compressor or a cooling system is used in order to collect isobutylene as a liquefied gas, and consequently, installation cost and energy cost become very large and hence this is economically unfavorable.

Patent Document 1: Japanese Patent Application Laid-Open No. Sho 63-135,352

Patent Document 2: Japanese Patent Application Laid-Open No. Sho 62-63,544

Patent Document 3: U.S. Pat. No. 4,012,456

Patent Document 4: Japanese Patent Application Laid-Open No. Sho 54-135,710

Patent Document 5: Japanese Patent Application Laid-Open No. Sho 54-138,506

Patent Document 6: U.S. Pat. No. 4,036,905

Patent Document 7: Japanese Patent Application Laid-Open No. Sho 47-13,250

DISCLOSURE OF INVENTION

Problem to be Solved by the Invention

It is an object of the present invention to provide a method for synthesizing t-butyl (meth)acrylate inexpensively from inexpensive t-butyl alcohol.

Means for Solving the Problem

The present inventors have diligently researched each of a dehydration decomposition reaction of t-butyl alcohol to produce isobutylene and an addition reaction between (meth)acrylic acid and isobutylene and have obtained the following findings.

1. By removing water contained in isobutylene produced in the foregoing dehydration decomposition step, t-butyl (meth)acrylate is produced in a high yield in the subsequent step of an addition of isobutylene to (meth)acrylic acid.

2. A large part of water contained in isobutylene obtained by way of the dehydration decomposition step can be removed by a simple separation operation (such as condensation).

3. When the separation operation in the foregoing 2 is performed, a large part of an isobutylene oligomer produced in the dehydration reaction and unreacted alcohol are removed simultaneously, and further, among condensed components, the isobutylene oligomer which is an unnecessary component and moisture containing the unreacted alcohol are separated by forming separate phases, and hence useful t-butyl alcohol can be recovered and reused easily.

4. The addition reaction can be satisfactorily performed on an acidic catalyst by contacting and dissolving crude isobutylene gas to a liquid containing (meth)acrylic acid which is a raw material after the foregoing simple separation operation because the condensable components in the produced gas of the dehydration decomposition reaction are similar to the product components in side reactions of the addition reaction.

Further, they have found a method of freezing point depression of a carboxylic acid caused by dissolving isobutylene in the step of contacting and dissolving isobutylene gas and a method of increasing solubility of isobutylene caused by recycling a product of the addition reaction to the step of contacting and dissolving isobutylene gas, and hence have found a method of remarkably increasing absorption efficiency of the crude isobutylene and thus performing the addition reaction efficiently.

Further, they have found a method of effectively utilizing unreacted t-butyl alcohol in the dehydration decomposition reaction and an unreacted olefin in the addition reaction.

The present invention has been completed based upon the foregoing findings. Namely, the present invention is a method for synthesizing t-butyl (meth)acrylate by performing an addition reaction between isobutylene and (meth)acrylic acid in the presence of an acidic catalyst, the method including the steps of:

(A) performing a dehydration decomposition reaction of t-butyl alcohol in the presence of a first acidic catalyst;

(B) obtaining crude isobutylene gas by separating at least water from a produced gas obtained in the step A;

(C) absorbing the crude isobutylene gas in an absorption solvent containing (meth)acrylic acid; and (D) producing t-butyl (meth)acrylate by performing the addition reaction by bringing the absorption solvent which has absorbed the crude isobutylene into contact with a second acidic catalyst.

Now, in the present invention, (meth)acrylic acid is a general term for acrylic acid and methacrylic acid.

In the step B, it is preferable to perform the step of:

(b) cooling the produced gas obtained in the step A, and separating water, unreacted t-butyl alcohol and an isobutylene oligomer which are contained in the produced gas by condensation.

It is preferable that the foregoing method further include the step of:

(E) separating a condensate separated in the step (b) into two phases and supplying a lower layer of the two phases to the dehydration decomposition reaction in the step A.

In the step C, it is preferable to perform the step of:

(c) supplying the crude isobutylene gas obtained in the step B to a gas-liquid contactor, cooling a liquid obtained by adding (meth)acrylic acid to a bottoms liquid of the gas-liquid contactor, supplying part of the resultant cooled liquid to the gas-liquid contactor to cause gas-liquid contact with the crude isobutylene gas, and supplying the remainder of the cooled liquid to the step D.

It is preferable that the foregoing method further include the step of:

(F) supplying part of the t-butyl (meth)acrylate obtained in the step D to the step C.

It is preferable that the foregoing method further include the step of:

(G) recovering unreacted isobutylene from a produced liquid obtained in the step D and supplying the unreacted isobutylene to the step B.

In the foregoing step G, the unreacted isobutylene can be recovered by heating, depressurizing and/or distilling a produced liquid obtained in the foregoing step D.

It is preferable that the dehydration decomposition reaction in the step A, the absorption in the step C and the addition reaction in the step D be performed under the pressure in the range of from 0 MPa-G to less than 1 MPa-G.

Here, G of the pressure unit means gauge pressure.

EFFECT OF THE INVENTION

According to the present invention, t-butyl (meth)acrylate can be inexpensively synthesized because expensive isobutylene is not used and crude isobutylene gas obtained from inexpensive t-butyl alcohol is used as a raw material for the addition reaction without any high-degree refining and thus a raw material cost is reduced.

EXPLANATION OF NUMERALS

1: Reaction tube (packed with a silica-alumina catalyst)
2: Condenser
3: Isobutylene-dissolving tank
4: Column (packed with a strongly acidic ion exchange resin)
5: Evaporator
6: T-butyl alcohol aqueous solution supply pump
7: Methacrylic acid supply pump
8: Condensate liquid-receiving tank
9: Absorption column
10: Circulating pump
11: Heat exchanger
12: Heating deaeration tank
13: Reduced-pressure deaeration tank
20: Condenser
21: Condenser
22: Blower

BEST MODE FOR CARRYING OUT THE INVENTION

Hereinafter, the present invention will be explained in more detail with respect to each step.

(Step A: A Dehydration Decomposition Step)

In the dehydration decomposition step A, a produced gas containing isobutylene is obtained by converting t-butyl alcohol which is a raw material to isobutylene. As a method of doing this, any method in which t-butyl alcohol which is a raw material can be supplied in a gas state or in a liquid state to a reactor having a first acidic catalyst (an acidic catalyst for promoting a dehydration decomposition reaction) and isobutylene to be produced can be taken out of the reaction system can be adopted as appropriate. As the first acidic catalyst, any catalysts which can convert t-butyl alcohol which is a raw material to isobutylene by dehydration can be used, however, a strongly acidic catalyst is preferable and a solid acid catalyst is more preferable because a reaction liquid and the catalyst can be easily separated. For example, sulfuric acid can be used, and as the solid acid catalyst, a solid phosphoric acid, activated alumina and silica-alumina can be used.

The dehydration decomposition reaction is an equilibrium reaction and consequently, the reaction is continuously advanced if isobutylene which is a product could be taken out of the reaction system. It is preferable to perform the dehydration decomposition reaction at 100 to 450° C. to shift the equilibrium to a production side of isobutylene. For example, it is possible to use a method in which a reaction device of external circulation type having a reactor packed with the first acidic catalyst is provided with distillation equipment, t-butyl alcohol is directly supplied to the reactor under heating while produced isobutylene is taken out of the system by evaporation, a remainder of reaction liquid is introduced into the distillation equipment, and mainly t-butyl alcohol and an isobutylene oligomer are separated as evaporating components and supplied again to the reactor. Or, it is possible to use a method in which t-butyl alcohol is supplied to an evaporator to be evaporated, and a dehydration decomposition reaction of t-butyl alcohol is performed in a gas state on a strongly acidic solid catalyst.

(Step B: A Water Removing Step)

In the step B, isobutylene is separated from the isobutylene-containing produced gas produced in the dehydration decomposition reaction to obtain crude isobutylene gas. At that time, it is preferable to separate isobutylene as a gas and the other components as liquids. A higher isobutylene content of the crude isobutylene to be obtained is preferable, however, it is not particularly necessary to remove isobutylene oligomer and t-butyl alcohol, which do not exert unfavorable effect on the addition reaction, to a degree. The main purpose of this step is to remove water which exerts unfavorable effect on the addition reaction, and it is preferable to remove at least water. Water content in the crude isobutylene gas is preferably about 1% by mass or less.

For this separation, water can be separated through condensation by cooling the produced gas obtained in the step A. A general method for removing moisture other than condensation such as adsorption, absorption, or freezing may be used. With the view of reusing unreacted t-butyl alcohol in the dehydration decomposition reaction, it is preferable to partly condense and separate water, unreacted t-butyl alcohol and isobutylene oligomer from the produced gas of the dehydration decomposition reaction by condensing the produced gas at 0° C. or more and 80° C. or less, more preferably at 2° C. or more and 80° C. or less in order to avoid freezing of moisture at a surface of condenser (step (b)).

(Step E: Recycle of t-Butyl Alcohol)

In order to reuse t-butyl alcohol in a liquid containing water, t-butyl alcohol, and isobutylene oligomer, the liquid being separated in the step B (or b), it is preferable that an ordinary two-phase separation such as decantation of the liquid be performed and water phase side, namely a lower layer, be supplied and recycled to the dehydration decomposition reaction, after excess water be removed, when necessary, with a simple distillation operation. At this time, impurities can be effectively removed by discharging an upper layer (oil phase) containing the isobutylene oligomer. Further, the liquid may be supplied to the dehydration decomposition reaction, without using decantation or the like, after excess water is removed with a simple distillation operation such as flash distillation or utilization of distillation still.

(Step C: An Absorption Step)

The crude isobutylene gas obtained in the step B is caused to be absorbed in an absorption solvent containing (meth)acrylic acid which is to be a raw material for the addition reaction in the step C. As a method of doing this, a method in which isobutylene gas can be absorbed in (meth)acrylic acid can be properly adopted. At this time, a gas-liquid contactor like, for example, a gas-liquid integral contactor such as a packed column, a wetted wall column, a bubble column, or a spray tower, or a gas-liquid tray type contactor such as a tray type distillation column can be used. It is preferable to use the gas-liquid integral contactor to perform absorption more effectively.

In the gas-liquid contactor, it is preferable that a liquid to be supplied or circulated to the gas-liquid contactor be cooled from the viewpoint of improving efficiency of dissolution of isobutylene gas. In particular, it is preferable to add (meth)acrylic acid to a bottoms liquid of the gas-liquid contactor and to cool and circulate this liquid to supply to the gas-liquid contactor because freezing point of (meth)acrylic acid is high and it is difficult to supply (meth)acrylic acid after it is cooled.

Namely, it is preferable that the step (c) be performed, more exactly, the crude isobutylene gas obtained in the foregoing step B be supplied to a gas-liquid contactor, and a liquid obtained by adding (meth)acrylic acid to the bottoms liquid of the gas-liquid contactor be cooled, and part of the resultant cooled liquid be supplied to the foregoing gas-liquid contactor as an absorption solvent, and the remainder of the cooled liquid be supplied to the foregoing step D.

By lowering the freezing point of (meth)acrylic acid by mixing (meth)acrylic acid and the bottoms liquid of the gas-liquid contactor, and by cooling the resultant mixed liquid and using this as an absorption solvent, a temperature inside the gas-liquid contactor can be lowered to improve an absorption efficiency of gaseous substances while avoiding freezing of (meth)acrylic acid. For example, loss of isobutylene from a vent of absorbing column can be reduced as well as isobutylene concentration in the absorption solvent containing (meth)acrylic acid can be increased. Consequently, rate of the addition reaction can be improved and thus productivity of the addition reaction can be improved. Further, high absorption efficiency can be obtained under a low pressure condition and hence there is no necessity for making the system work under high pressure so that there is no necessity for using expensive pressure vessels. As a result, it is possible to synthesize t-butyl (meth)acrylate more inexpensively.

Temperature of the foregoing mixed and cooled liquid (a liquid obtained by mixing (meth)acrylic acid and the bottoms liquid of the gas-liquid contactor and by cooling the resultant liquid) is preferably −10 to 25° C. Further, a rate of isobutylene dissolution in (meth)acrylic acid inside the gas-liquid contactor (expressed by the following equation (1)) is preferably 10 to 100% and more preferably 20 to 100%.

(Equation (1))

(Rate of isobutylene dissolution)=1−{(the amount of isobutylene released out of the system from the gas-liquid contactor)/(the amount of isobutylene supplied to the absorption column)}  Equation (1)

As the amount of the foregoing mixed and cooled liquid to be supplied to the gas-liquid contactor becomes large, temperature inside the gas-liquid contactor can be more lowered because isobutylene concentration in the supplied liquid becomes high and hence the freezing point of (meth)acrylic acid is lowered, however, this causes a size of the device to increase because a load of the mixed and cooled liquid becomes large. Therefore, a circulation ratio of the mixed and cooled liquid is, being summed up with an amount of supply of t-butyl (meth)acrylate in the step F which will be mentioned later, preferably within the range of form 0.01 times to 100 times by mass ratio to (meth)acrylic acid to be supplied.

In order to add (meth)acrylic acid to the bottoms liquid of the gas-liquid contactor, (meth)acrylic acid may be directly supplied to the bottom of the gas-liquid contactor or may be added to the bottoms liquid which has previously been taken out of the gas-liquid contactor.

Further, in order to increase absorption efficiency of the gaseous substances, another absorption solvent in addition to (meth)acrylic acid can also be used. This absorption solvent can be properly selected from those having vapor pressures which are sufficient to avoid their mixing into t-butyl (meth) acrylate which is a product when a target t-butyl (meth)acrylate is obtained by distillation and the like and those having no reactivity in the addition reaction. For example, sulfone solvents such as sulfolane, 2-methyl sulfolane, 3-methyl sulfolane, 3-propyl sulfolane, 3-butyl sulfolane, dimethyl sulfone, diethyl sulfone, methylethyl sulfone, dipropyl sulfone, sulfonal, and trional, low-boiling solvents such as n-hexane, benzene, chloroform, and methylene chloride, and high-boiling solvents such as isopropyl benzene, diethyl benzene, and amyl benzene can be used.

As an operational pressure of the absorption, it is more preferable to effectively dissolve gaseous isobutylene into a liquid under pressure, however, expensive system designs and system materials may be needed depending on a pressure, which may degrade economic feasibility, and hence it is preferable in the present invention to perform the absorption under about atmospheric pressure.

(Step D: An Addition Reaction Step)

Step D is performed, in which t-butyl (meth)acrylate is produced by performing the foregoing addition reaction by bringing the absorption solvent which has absorbed the crude isobutylene into contact with a second acidic catalyst (an acidic catalyst for promoting an addition reaction). For example, a liquid obtained by contacting and dissolving crude isobutylene to an absorption solvent containing (meth)acrylic acid which is a raw material is introduced at a law temperature into a reactor holding a second acidic catalyst and an addition reaction is performed. As a reaction temperature, it is preferably within the range of from –20° C. to 20° C. because, as the reaction temperature becomes lower, a side reaction (polymerization reaction of isobutylene) is more suppressed, on the other hand, reaction rate is reduced and reactor efficiency is lowered.

As the second acidic catalyst, any one of a homogeneous catalyst and a solid catalyst may be used, however, an acidic solid catalyst is preferable, a strongly acidic solid catalyst is more preferable, and an ion exchange resin is particularly preferable. As a strongly acidic ion exchange resin, a crosslinked ion exchange resin containing a sulfonic acid group is preferable because it has high activity. For example, Amberlyst-15 (trade name), Amberlite IR-200cH (trade name) manufactured by Rohm and Haas Co., Lewatit SPC-108 (trade name), Lewatit SPC-118 (trade name) manufactured by BayerAG, and DiaionRCP-150H (trade name) manufactured by Mitsubishi Chemical Corporation can be suitably used.

(Step G: An Isobutylene Recovery Step)

An isobutylene utilization may be improved by recovering unreacted isobutylene from the produced liquid of the addition reaction obtained in the step D and using it again as a raw material of the addition reaction. This recovering can be performed by heating, depressurizing or distilling the produced liquid obtained in the step D, or in combination of these procedures. The recovered isobutylene can be reused in the addition reaction after its pressure is controlled when necessary.

In particular, it is preferable that the recovered isobutylene be supplied to the step B and recycled. For example, the recovered isobutylene can be introduced into a portion located between an outlet of the dehydration decomposition reaction and an inlet of a heat exchanger for condensation and the like. Consequently, t-butyl alcohol contained in the recovered isobutylene is separated in the step B (or b) and the recovered isobutylene can be refined. Further, t-butyl alcohol contained in the recovered isobutylene can be effectively reused in the dehydration decomposition reaction of the step A when t-butyl alcohol contained in a liquid separated in the step B is supplied to the step A and recycled to the dehydration decomposition reaction (for example, when the step E is performed).

(Step F: A t-Butyl (Meth)Acrylate Recovery Step)

Step F may be performed in which part of the t-butyl (meth)acrylate obtained in the step D is supplied to the foregoing step C and recycled as the absorption solvent. As the ratio of t-butyl (meth)acrylate in (meth)acrylic acid becomes higher, solubility of isobutylene to the absorption solvent is improved and absorption efficiency is increased because t-butyl (meth)acrylate has high affinity for isobutylene. Therefore, for example, loss of isobutylene from a vent of an absorption column can be reduced. Besides, the addition reaction rate can be increased and thus productivity of the addition reaction can be improved by an increase of isobutylene concentration in the absorption solvent containing (meth)acrylic acid. As a result, t-butyl (meth)acrylate can be synthesized more inexpensively. It is not necessary to separate t-butyl (meth)acrylate from the produced liquid obtained in the step D and to supply it to the step C, but part of the produced liquid obtained in the step D may be supplied to the step C as an absorption solvent. Although solubility of isobutylene to the absorption solvent is improved as an amount of t-butyl (meth)acrylate to be supplied to the step C is increased, this causes a decrease of a reaction rate in the step D in addition to an increase of an absorption size in the step C owing to an increase of a load of the liquid in the step C. Therefore, an amount of supply of t-butyl (meth)acrylate in the step F is, being summed up with an amount of supply of the foregoing bottoms liquid of the gas-liquid contactor in the step C, preferably within the range of from 0.01 times to 100 times by mass ratio to (meth)acrylic acid to be supplied to the step C.

According to the present invention, the dehydration decomposition reaction in the foregoing step A, the absorption in the step C and the addition reaction in the step D can be performed under about atmospheric pressure (namely, a gauge pressure in the range of from 0 MPa-G to less than 1 MPa-G) because absorption efficiency of isobutylene in the step C is high. For example, it is possible to perform a reaction or an absorption without pressurizing in particular, at a pressure which is higher than atmospheric pressure by an amount equivalent to a pressure drop caused by transporting a fluid. Consequently, high-pressure equipment become unnecessary, installation cost can be suppressed, and t-butyl (meth) acrylate can be synthesized more inexpensively.

A target t-butyl (meth)acrylate can be obtained from addition reaction products, by performing, when desired, a refining step such as distilling using at least one distillation equipment after unreacted isobutylene is recovered. At this time, a liquid in which unreacted (meth)acrylic acid is concentrated by removing high-boiling residue may be recycled to the addition reaction when it is needed.

Further, in the foregoing refining step, a polymerization inhibitor may be used.

The polymerization inhibitor can be properly selected from publicly known polymerization inhibitors which can prevent polymerization of (meth)acrylic acid and t-butyl (meth)acrylate. As the polymerization inhibitor, for example, a quinone compound such as hydroquinone or hydroquinone monomethyl ether; an amine compound such as hydroxy N,N'-diisopropyl paraphenylenediamine, N,N'-di-2-naphtyl paraphenylenediamine, N-phenyl-N'-(1,3-dimethylbutyl) paraphenylenediamine, or phenothiazine; an N-oxyl compound such as 4-hydroxy-2,2,6,6-tetramethylpiperidine-N-oxyl or 4-benzoyloxy-2,2,6,6-tetramethylpiperidine-N-oxyl; or an N-oxyl compound exemplified by the following formula (I) can be listed.

Formula (1)

(In the above formula, n represents an integer of 0 to 18. $R^1$ and $R^2$ represent a hydrogen atom, respectively, or one represents a hydrogen atom and the other represents a methyl group. $R^3$, $R^4$, $R^5$ and $R^6$ independently represent a straight-chain or a branched alkyl group, respectively. $R^7$ represents a hydrogen atom or a (meth)acryloyl group.)

Among them, 4-benzoyloxy-2,2,6,6-tetramethylpiperidine-N-oxyl, or a compound represented by the foregoing formula (I) in which $R^1$, $R^2$ and $R^7$ are hydrogen atoms and $R^3$ to $R^6$ are methyl groups and n is any one of 1 to 12 is preferable owing to their high boiling points.

The polymerization inhibitor can be used alone or in combination of two or more kinds.

The polymerization inhibitor can be supplied to the refining step in the form as it is or in a solution state. In particular, when inhibiting polymerization of t-butyl (meth)acrylate in a distillation column is desired, a method in which the polymerization inhibitor is dissolved in a material contained in the distillation system and the resultant material is supplied to a top or a middle stage of the distillation column is preferable.

Further, in the refining step, a molecular oxygen or air may be caused to coexist when it is needed with the view of enhancing polymerization-inhibiting effect. This can be easily performed by a method such as an air bubbling method.

In the present invention, it is preferable that each step be performed continuously from the viewpoint of productivity.

EXAMPLES

Hereinafter, the method of the present invention will be explained by way of the following examples, however, the present invention is not limited by these examples.

Example 1

Figure 1:
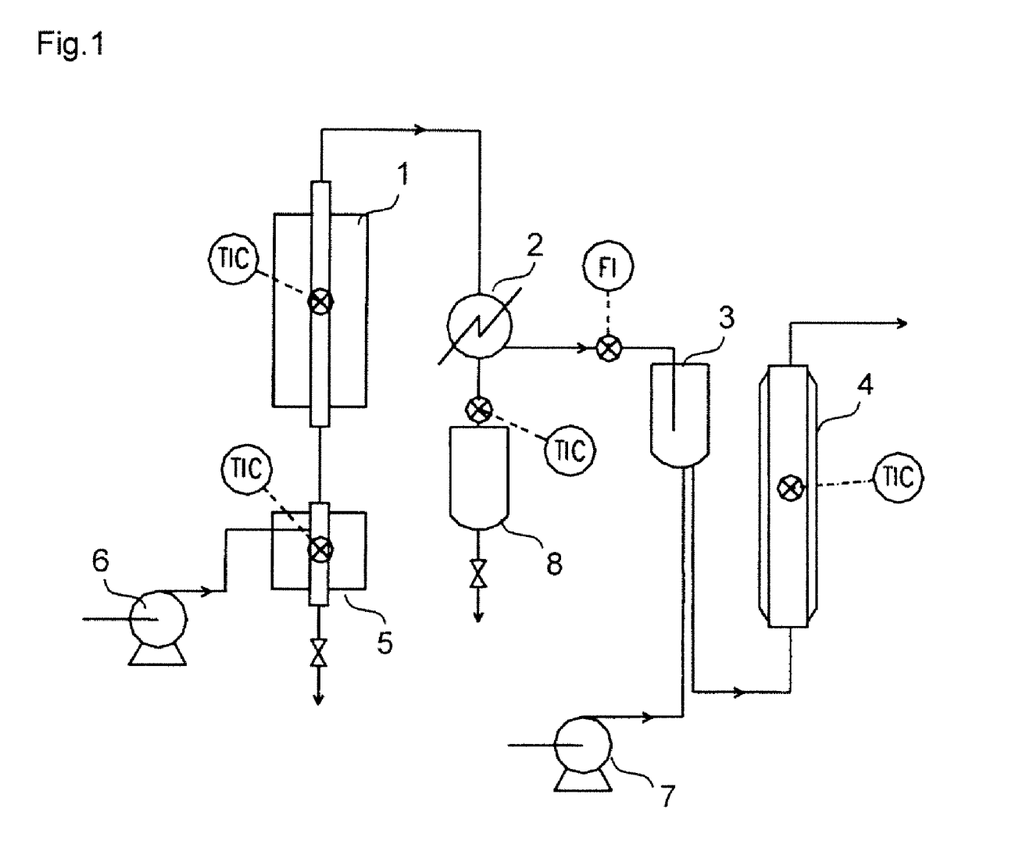
FIG. 1 is a flow diagram showing an example of equipment that can carry out the method of the present invention.

FIG. 1 shows a flow diagram of an example of equipment that can carry out the method of the present invention.

A molded silica-alumina catalyst N631HN (trade name; manufactured by Nikki Chemical Co., Ltd.; 5 mm in diameter×5 mm in length) on sale was packed in a stainless steel tube having an inside diameter of 13 mm and a length of 115 mm, to obtain reaction tube 1. To evaporator 5, 86.5% by mass ratio of t-butyl alcohol aqueous solution was supplied at a rate of 0.196 g/min using t-butyl alcohol aqueous solution supply pump 6, all of which was evaporated and passed through the reaction tube 1, and a dehydration decomposition reaction was continuously performed at 160° C. When the reaction was presumed to have reached a steady state, reaction gas was sampled and analyzed with gas chromatography to obtain results of a conversion of 93.7% based on t-butyl alcohol and an isobutylene yield of 85.8%.

A produced gas of the dehydration decomposition reaction was introduced into condenser 2 and condensed components were separated while controlling a flow rate of coolant to adjust the temperature of condensate liquid at 2° C. A composition of a crude isobutylene gas after the condensed components were separated is shown in Table 1.

TABLE 1

| Composition of crude isobutylene gas | |
|---|---|
| Isobutylene | 98.4% by mass |
| T-butyl alcohol | 1.4% by mass |
| Water | 0.2% by mass |
| Isobutylene dimer | Not detected |

The condensate liquid which was condensed and separated in condenser 2 was received in condensate liquid-receiving tank 8 and discharged from the bottom of the condensate liquid-receiving tank 8. A composition of the condensate liquid was 87.3% by mass of water, 12.1% by mass of t-butyl alcohol, and 0.6% by mass of isobutylene.

The crude isobutylene gas thus obtained was continuously introduced into isobutylene-dissolving tank 3 which was open to atmosphere. To the isobutylene-dissolving tank 3, methacrylic acid cooled to 18° C. was continuously introduced at a rate of 0.17 g/min using methacrylic acid supply pump 7. A rate of isobutylene dissolution in the isobutylene-dissolving tank 3 was 15.51%. Unabsorbed isobutylene in the isobutylene-dissolving tank 3 was lost from a vent of the isobutylene dissolving tank 3. A liquid in which the crude isobutylene gas obtained was dissolved was introduced into jacketed glass column 4 having an inside diameter of 20 mm and a length of 1,000 mm and packed with a strongly acidic ion exchange resin Amberlite IR-200cH (trade name, manufactured by Rohm and Haas Co.), and an addition reaction was performed. Inside of the jacketed glass column 4 was kept at 5° C. by introducing cold water into the jacket. An yield of t-butyl (meth)acrylate was 12.29% based on t-butyl alcohol supplied.

Example 2

Figure 2:
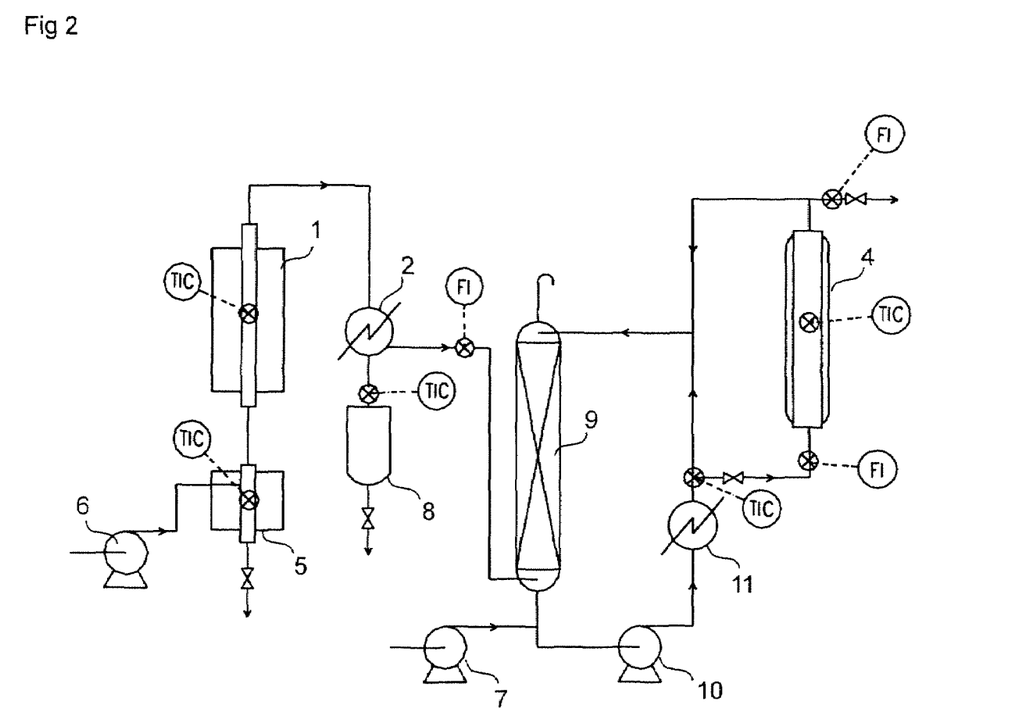
FIG. 2 is a flow diagram showing another example of equipment that can carry out the method of the present invention.

As a substitution of the isobutylene-dissolving tank 3 used in Example 1, absorption column 9 which was equivalent to number of theoretical plates of 5 and open to atmosphere was provided. FIG. 2 shows a flow diagram of a test apparatus.

The same procedures of a dehydration decomposition reaction and a separation of condensed components as in Example 1 were performed and crude isobutylene was obtained.

Crude isobutylene gas was supplied to the bottom of the absorption column 9. Methacrylic acid, temperature of which was 18° C., was supplied to a line located downstream of the bottom of the absorption column 9 at a rate of 0.17 g/min and a bottom liquid of the absorption column 9 and methacrylic acid were mixed. The resultant mixed liquid, freezing point of which was lowered as compared with methacrylic acid owing to dissolution of isobutylene (the freezing point of methacrylic acid being about 15° C.), was passed through heat exchanger 11 using circulation pump 10 and cooled to 4° C., and part of an outlet liquid of the heat exchanger 11 was recycled to the top of the absorption column 9 at a rate of 0.84 g/min. A rate of isobutylene dissolution in the absorption column 9 was 30.86%. Unabsorbed isobutylene in the absorption column 9 was lost from a vent of the absorption column 9.

The remainder of the outlet liquid of the heat exchanger 11 was passed through the same jacketed glass column 4 packed with the ion exchange resin as in Example 1 and an addition reaction was performed at 5° C. Although there is shown a recycle line from the glass column 4 to the absorption column 9 in FIG. 2, recycle was not performed in this example.

An yield of t-butyl (meth)acrylate was 18.90% based on t-butyl alcohol supplied.

Example 3

Using equipment shown in FIG. 2, recycling from the jacketed glass column 4 to the top of the absorption column 9 was performed in addition to the same operations as in Example 2.

Recycling from the bottom of the absorption column 9 to the top of the absorption column 9 without passing the jacketed glass column 4 was performed at a rate of 1.60 g/min, and recycling from the outlet of the jacketed glass column 4 to the top of the absorption column 9 was performed at a rate of 0.16 g/min. The other conditions were the same as in Example 2.

As a result, a rate of isobutylene dissolution in the absorption column 9 was 56.34% (unabsorbed isobutylene in the absorption column 9 being lost from a vent of the absorption column 9) and an yield of t-butyl (meth)acrylate was 21.48% based on t-butyl alcohol supplied.

Example 4

Figure 3:
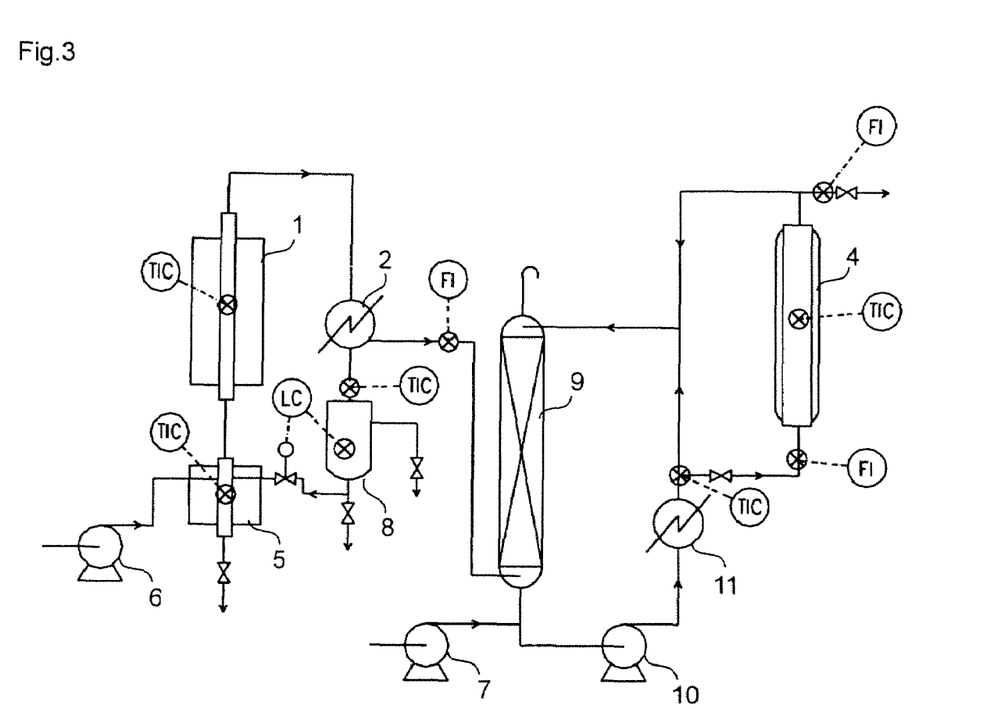
FIG. 3 is a flow diagram showing another example of equipment that can carry out the method of the present invention.

In addition to the equipment of Example 3, a line was provided to the condensate liquid-receiving tank 8, the line supplying all of a lower layer (water phase) obtained by decantation of the condensate to evaporator 5, and a continuous operation was performed (FIG. 3).

To evaporator 5, 86.5% by mass of t-butyl alcohol aqueous solution was supplied at a rate of 0.196 g/min, in the same manner as in Example 3, and besides, the water phase of the condensate liquid-receiving tank 8 was supplied, and the resultant evaporated and preheated gas was passed through the reaction tube 1 to perform a dehydration decomposition reaction at 160° C. Water, containing about 500 ppm by mass of t-butyl alcohol, accumulated at the bottom of the evaporator 5, was successively taken out at a rate of 0.06 to 0.07 g/min. An upper layer (organic layer) of the condensate liquid-receiving tank 8 was discharged through overflow. As a result, an yield of isobutylene was 91.4% based on t-butyl alcohol supplied.

Crude isobutylene gas thus obtained was introduced into condenser 2 and condensed components were separated at 2° C. in the same manner as in Example 3, and then supplied to the bottom of the absorption column 9. Methacrylic acid, temperature of which was 18° C., was added to the bottom liquid of the absorption column 9 at a rate of 0.17 g/min and the resultant liquid was cooled to 4° C. with the heat exchanger 11, and part of an outlet liquid of the heat exchanger 11 was recycled to the top of the absorption column 9 at a rate of 1.60 g/min. The remainder of the outlet liquid of the heat exchanger 11 was passed through the same jacketed glass column 4 packed with the strongly acidic ion exchange resin as in Example 3 and an addition reaction was performed at 5° C. Part of an outlet liquid of the jacketed glass column 4 was recycled to the top of the absorption column 9 at a rate of 0.16 g/min.

As a result, an yield of t-butyl (meth)acrylate was 21.56% based on t-butyl alcohol supplied.

Example 5

Figure 4:
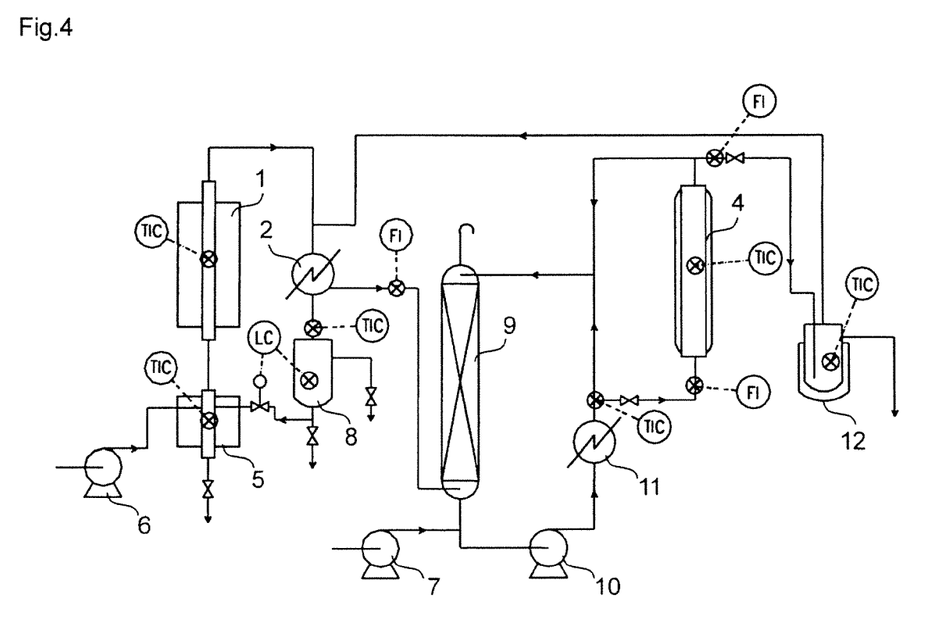
FIG. 4 is a flow diagram showing another example of equipment that can carry out the method of the present invention.

In addition to the procedures of Example 4, a step in which unreacted isobutylene in the addition reaction was recovered by heating and recycled to the absorption column 9 was added (FIG. 4).

As will be mentioned later, the same procedure as in Example 4 was performed and crude isobutylene gas was obtained and supplied to the bottom of the absorption column 9 except that isobutylene gas removed at heating deaeration tank 12 was supplied to heat exchanger 2.

Methacrylic acid, temperature of which was 18° C., was added to the bottom liquid of the absorption column 9 at a rate of 0.34 g/min and the resultant liquid was cooled to 4° C. with the heat exchanger 11, and part of an outlet liquid of the heat exchanger 11 was recycled to the top of the absorption column 9 at a rate of 13.40 g/min. The remainder of the outlet liquid of the heat exchanger 11 was passed through the same jacketed glass column 4 packed with the strongly acidic ion exchange resin as in Example 4 and an addition reaction was performed at 5° C. Part of an outlet liquid of the jacketed glass column 4 was recycled to the top of the absorption column 9 at a rate of 2.68 g/min. The remainder of the outlet liquid of the jacketed glass column 4 was introduced into the heating deaeration tank 12 and dissolved isobutylene was removed at 70° C., and the resultant removed isobutylene gas was introduced into the heat exchanger (condenser) 2.

As a result, a rate of isobutylene dissolution in the absorption column 9 became 98.79%, namely almost the whole quantity of isobutylene was recovered in the absorption column 9, and an yield of t-butyl (meth)acrylate was 35.87% based on t-butyl alcohol supplied.

Example 6

Figure 5:
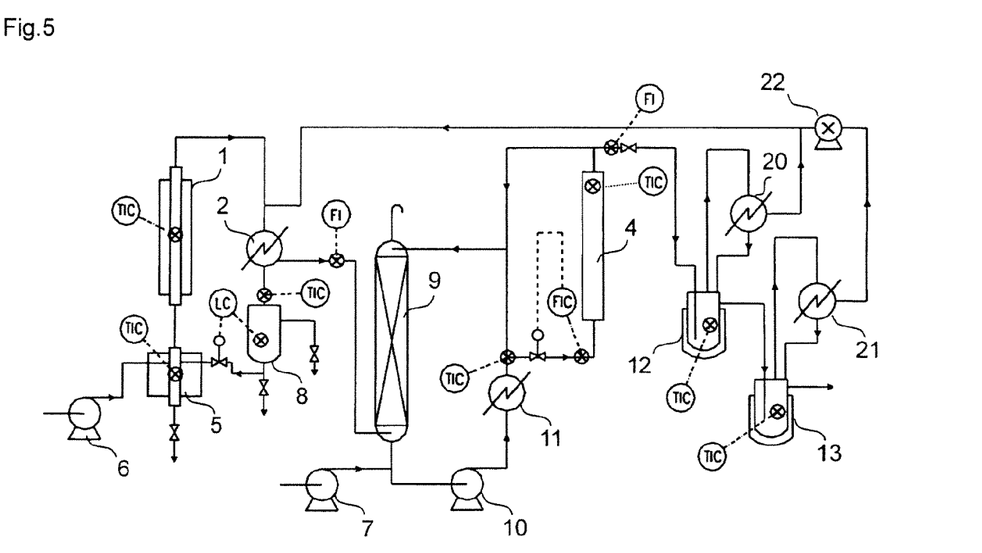
FIG. 5 is a flow diagram showing another example of equipment that can carry out the method of the present invention.

Test apparatus shown in FIG. 5 was used.
The foregoing molded silica-alumina catalyst N631HN and an inactive support (spherical glass, 5 mm in diameter) were mixed and packed by the same amount (based on a bulk volume), respectively, in a stainless steel tube having an inside diameter of 22.5 mm and a length of 2,100 mm to obtain reaction tube 1.

To evaporator 5, 86.5% by mass of t-butyl alcohol aqueous solution was supplied at a rate of 0.206 kg/hr, and besides, the water phase of the condensate liquid-receiving tank 8 was supplied, and the resultant evaporated and preheated gas was passed through the reaction tube 1 to perform a dehydration decomposition reaction at 160° C. Water accumulated at the bottom of the evaporator 5 was successively taken out. An upper layer (organic layer) of the condensate liquid-receiving tank 8 was discharged through overflow. As a result, an yield of isobutylene was 97.8% based on t-butyl alcohol supplied.

Crude isobutylene gas thus obtained was introduced into condenser 2 and condensed components were separated at 2° C., and then supplied to the bottom of the absorption column 9 which was open to atmosphere. Methacrylic acid, temperature of which was 18° C., was added to the bottom liquid of the absorption column 9 at a rate of 0.776 kg/hr and the resultant liquid was cooled to 4° C. with the heat exchanger 11. An outlet liquid of the heat exchanger 11 was passed through a stainless steel column 4 having a diameter of 30 mm and a length of 1,850 mm and packed with a strongly acidic ion exchange resin (the foregoing Amberlite IR-200cH) and an addition reaction was performed. Part of an outlet liquid of the stainless steel column 4 was recycled to the top of the absorption column 9 at a rate of 17.32 kg/hr. The remainder of the outlet liquid of the stainless steel column 4 was introduced into the heating deaeration tank 12. Direct recycling from the heat exchanger 11 to the absorption column 9 was not performed. At the heating deaeration tank 12, part of unreacted isobutylene was deaerated and recovered by keeping an inside temperature at 70° C. through adjusting flow rate of steam for heating and by refluxing with equipped condenser 20 which used a tap water as a coolant. The resultant produced liquid of the addition reaction after deaeration was further introduced into reduced-pressure deaeration tank 13, where unreacted isobutylene was deaerated and recovered by keeping the inside temperature at 70° C. through adjusting flow rate of steam for heating and by refluxing with equipped condenser 21 which used a tap water as a coolant and further by keeping the inside pressure at 80 mmHg (11 kPa) through adjusting a leak valve of blower 22. Isobutylene gas recovered at the heating deaeration tank 12 and the reduced-pressure deaeration tank 13 was recycled to the inlet of the condenser 2.

As a result, almost the whole quantity of isobutylene was recovered in the absorption column 9, and an yield of t-butyl (meth)acrylate reached 96.0% based on t-butyl alcohol supplied.

INDUSTRIAL APPLICABILITY

T-butyl (meth)acrylate is widely used in industry, for example, as raw materials for chemicals.

What is claimed is:

1. A method for synthesizing t-butyl (meth)acrylate by performing an addition reaction between isobutylene and (meth)acrylic acid in the presence of an acidic catalyst, the method comprising:
    (A) performing a dehydration decomposition reaction of t-butyl alcohol in the presence of a first acidic catalyst;
    (B) obtaining a crude t-butyl alcohol-containing isobutylene gas by separating at least water from a produced gas obtained in the step A to form the t-butyl alcohol-containing crude isobutylene gas;
    (C) absorbing the t-butyl alcohol-containing crude isobutylene gas in an absorption solvent containing (meth)acrylic acid; and
    (D) producing t-butyl (meth)acrylate by performing the addition reaction by bringing the absorption solvent which has absorbed the t-butyl alcohol-containing crude isobutylene gas into contact with a second acidic catalyst,
    wherein the t-butyl alcohol-containing crude isobutylene gas comprises 1% by mass or less of water.

2. The method according to claim 1, wherein the (B) obtaining comprises:
    (b) cooling the produced gas obtained in the step A, and separating water and an isobutylene oligomer which are contained in the produced gas by condensation.

3. The method according to claim 2, further comprising:
    (E) separating a condensate separated in (b) into two phases and supplying a lower layer of the two phases to the dehydration decomposition reaction in A.

4. The method according to claim 1, wherein the (C) absorbing comprises:
    (c) supplying the t-butyl alcohol-containing crude isobutylene gas obtained in B to a gas-liquid contactor, cooling a liquid obtained by adding (meth)acrylic acid to a bottoms liquid of the gas-liquid contactor, supplying part of the resultant cooled liquid to the gas-liquid contactor to cause gas-liquid contact with the crude isobutylene gas, and supplying the remainder of the cooled liquid to D.

5. The method according to claim 1, further comprising:
    (F) supplying part of the t-butyl (meth)acrylate obtained in D to C.

6. The method according to claim 1, further comprising:
    (G) recovering unreacted isobutylene gas from a produced liquid obtained in D and supplying the unreacted isobutylene to B.

7. The method according to claim 1, wherein the dehydration decomposition reaction in A, the absorption in C and the addition reaction in D are performed under the pressure in the range of from 0 MPa-G to less than 1 MPa-G.

8. The method according to claim 1, wherein the t-butyl alcohol-containing crude isobutylene gas from the (B) obtaining comprises isobutylene, t-butyl alcohol and water after the separating.

9. The method according to claim 1, wherein the t-butyl alcohol-containing crude isobutylene gas of the (C) absorbing comprises isobutylene, t-butyl alcohol and water.

10. The method according to claim 1, wherein the dehydration decomposition reaction of the (A) performing forms a produced gas that comprises an isobutylene oligomer and t-butyl alcohol.

11. The method according to claim 10, wherein the separating of the (B) obtaining is carried out without removing the isobutylene oligomer and the t-butyl alcohol from the produced gas.

12. The method according to claim 1, wherein the dehydration decomposition reaction of the (A) performing is carried out by evaporating a mixture of water and t-butyl alcohol to form a reaction gas and then subjecting the reaction gas to dehydration in a reaction tube comprising a catalyst.

13. The method according to claim 1, wherein the (C) absorbing is carried out by contacting and dissolving the t-butyl alcohol-containing crude isobutylene gas in (meth) acrylic acid to achieve a freezing point depression of the (meth)acrylic acid.

14. The method according to claim 1, wherein the t-butyl alcohol-containing crude isobutylene gas comprises 1.4% by mass or more of t-butyl alcohol.

15. The method according to claim 1, wherein the t-butyl alcohol-containing crude isobutylene gas comprises 1.4% by mass of t-butyl alcohol.

* * * * *

UNITED STATES PATENT AND TRADEMARK OFFICE
CERTIFICATE OF CORRECTION

PATENT NO. : 7,803,964 B2
APPLICATION NO. : 11/815664
DATED : September 28, 2010
INVENTOR(S) : Shigeho Tanaka et al.

Page 1 of 1

It is certified that error appears in the above-identified patent and that said Letters Patent is hereby corrected as shown below:

On the title page, Item (86), the Application Filing Date is incorrect. Item (86) should read:

-- (86) PCT No.:     PCT/JP2006/301993

§ 371 (c)(1),
(2), (4) Date:    Feb. 20, 2008 --

Signed and Sealed this
Ninth Day of August, 2011

David J. Kappos
*Director of the United States Patent and Trademark Office*